United States Patent

Dickman

Patent Number: 5,452,731
Date of Patent: Sep. 26, 1995

[54] DISPOSABLE, HYGROSCOPIC EAR PLUG INCLUDING TEAR-AWAY PORTION

[76] Inventor: Donald E. Dickman, 2222 S. Wayne St., Auburn, Ind. 46706

[21] Appl. No.: 329,650

[22] Filed: Oct. 25, 1994

[51] Int. Cl.⁶ .................................................. A61F 11/00
[52] U.S. Cl. .............................. 128/864; 2/209; 128/865
[58] Field of Search .................................. 128/864, 865; 2/209; 264/249, 292, 313, 510, 511, 516

[56] References Cited

U.S. PATENT DOCUMENTS

| | | | |
|---|---|---|---|
| 1,355,276 | 10/1920 | Schultz | 128/864 |
| 2,253,452 | 3/1941 | Powers et al. | |
| 2,446,707 | 8/1948 | Leight | 128/864 |
| 2,538,339 | 1/1951 | Thomas | |
| 2,574,288 | 11/1951 | Rosenblatt | 128/864 |
| 2,670,738 | 3/1954 | Gibbons | 128/864 |
| 2,824,558 | 2/1958 | Michael et al. | |
| 3,881,570 | 5/1975 | Lewis | 128/864 |
| 4,034,759 | 7/1977 | Haerr | |
| 4,094,315 | 6/1978 | Leight | 128/864 |
| 4,608,217 | 8/1986 | Csiki | 128/864 |
| 4,774,938 | 10/1988 | Leight | |
| 5,074,375 | 12/1991 | Grozil | 128/864 |
| 5,195,539 | 3/1993 | Dyrud et al. | |
| 5,203,352 | 4/1993 | Gardner | 128/864 |
| 5,249,309 | 10/1993 | Berg | 128/865 |

FOREIGN PATENT DOCUMENTS

| | | |
|---|---|---|
| 615458 | 2/1961 | Canada. |
| 1215869 | 4/1960 | France. |
| 1559694 | 3/1969 | France. |

*Primary Examiner*—Michael A. Brown
*Attorney, Agent, or Firm*—Richard C. Litman

[57] ABSTRACT

The present invention relates to a flexible, disposable ear plug which is capable of decreasing humidity levels from the environment within the inner ear of a user. The ear plug includes a resilient hygroscopic body and a removable integral tip which are both surrounded by a flexible waterproof casing. When the integral tip is removed from the body of the ear plug, a surface of the hygroscopic body of the ear plug is exposed. The ear plug is then compressed and inserted into the outer ear of a user such that the exposed hygroscopic surface of the ear plug is able to absorb moisture from within the ear.

7 Claims, 1 Drawing Sheet

DISPOSABLE, HYGROSCOPIC EAR PLUG INCLUDING TEAR-AWAY PORTION

BACKGROUND OF THE INVENTION

1. Field of the Invention

The present invention relates to resilient, disposable ear plugs which fit inside the outer ear canal of a user. More specifically, the present invention relates to a resilient ear plug having a hygroscopic core which will absorb moisture from the ear canal of a user.

2. Description of the Prior Art

A large variety of ear plugs suited for various sound-protection and health purposes have been described in the patent literature. For instance, U.S. Pat. No. 2,538,339, issued Jan. 16, 1951, to M. J. Thomas, describes a conventional insert-type ear plug. The ear plug has a resilient main body portion surrounding a stiff inner core. The ear plug is designed to keep noise, dust, and water from entering the ear canal.

U.S. Pat. No. 2,824,558, issued Feb. 25, 1958, to P. L. Michael et al. (Canadian Patent No. 615,458, issued Feb. 28, 1961), describes an insert-type ear plug in which a hydraulic liquid is used to adjust the dimensions of the ear plug after it has been set in place within the ear of a user. The shape of the ear plug can also be altered by mechanical means. The ability to alter the surface configuration of the ear plug ensures a secure fit of the plug within the ear of a user.

U.S. Pat. No. 4,034,759, issued Jul. 12, 1977, to R. H. Haerr, describes a device which is essentially a cylindrical tube of compressed, dehydrated, cellular material. In its dehydrated state, the tube is sufficiently rigid to be inserted within the ear canal of a human user. The wick is then be hydrated with a liquid medicament. This causes the wick to expand radially outward to substantially fill the ear canal. Once hydrated, the wick will press firmly against the walls of the ear canal, while the hollow of the tube will allow sound waves to pass through the ear canal to the inner ear.

U.S. Pat. No. 2,253,452, issued Mar. 3, 1981, to W. R. Powers et al., describes an ear plug assembly including two open-cell, resilient foam plug bodies connected by a flexible cord. The resilient foam material from which the plug bodies are formed has a slow recovery rate. The cord is inserted into each of the plug bodies by inserting it into preformed holes in the plug bodies. The preformed holes then close about cord due to the recovery of the open-celled foam.

U.S. Pat. No. 4,774,938, issued Oct. 4, 1988, to H. S. Leight, describes a single ear plug similar to that of Powers, above. The Leight plug includes a bullet-shaped body made from a slow-recovery, open-cell, resilient material. Here, however, the plug body is molded from a urethane foam material in such a manner that the open cells at the surface of the plug body are much smaller that the cells within the mass of the plug body. The small surface cells limits the amount of dirt which is adhered to the plug by handling, compressing and inserting it into the ear canal of a user.

Similar compressible ear plugs are described in French Patent Nos. 1,215.869, issued Apr. 21, 1960; and 1,559,694, issued Mar. 14, 1969.

U.S. Pat. No. 5,195,539, issued Mar. 23, 1993, to J. F. Dyrud et al., describes a device for compressing slow recovery earplugs prior to insertion into the ear canal of a user.

SUMMARY OF THE INVENTION

Many ear infections are caused, or are aggravated by, excessive moisture within the ear canal. This phenomenon has been popularly called "swimmers ear" due to the frequent ear infections which afflict some avid swimmers. Excess moisture within the ears provides a breeding ground for bacteria, which then multiply until the human host becomes symptomatic.

Left untreated, ear infections can be extremely debilitating, and in extreme cases even result in deafness. The most common symptoms are headaches, dizziness or spatial disorientation, diminution of aural acuity, and excessive discharges from the ear canal. The vast majority of these infections are easily treated using orally administered antibiotics.

However, many people, including those exposed to particularly damp environments, suffer from chronic ear infections. To effectively treat such chronic infections, it is necessary to limit any excess humidity within the ear canal. Any excess moisture within the ear canal provides a medium for bacteria to grow and multiply. By limiting the amount of moisture within the ear canal, chronic inner ear infections can be both prevented and treated.

The present invention is an ear plug which functions to decrease humidity levels with the ear canal of a user. The ear plug includes a resilient, hygroscopic body, and a removable tip which is integral with the body. Prior to use, both the tip and the body are hermetically sealed within a water-proof outer casing.

When the ear plug is to be used, the integral tip is torn from the body of the ear plug to activate the ear plug. This exposes a surface of the hygroscopic body of the ear plug. The ear plug is then compressed, inserted into the outer ear canal of a user such that the exposed hygroscopic surface is in contact with the space within the inner ear canal of the user, and released.

Once released, the resiliency of the ear plug will cause it to expand to form a friction fit within the ear canal, thereby sealing the ear canal from the ambient environment. The exposed hygroscopic surface will then function to absorb moisture from within the ear canal of the user.

The ear plug can be replaced with a fresh ear plug when the hygroscopic material of the ear plug is saturated. The old ear plug is simply discarded.

If desired, ear plugs according to the present invention may be formed in pairs by replacing the tip described above with the body of a second ear plug. In this arrangement, a pair of ear plugs would resemble a dumbbell. The two ends of the "dumbbell" would then be pulled apart to yield two activated ear plugs. Numerous permutations can be envisioned which would note deviate from the scope or spirit of this invention.

In view of the above discussion, it is a principal object of the present invention is to provide a resilient, disposable, and hygroscopic ear plug which will absorb moisture from within the ear canal of a user.

It is a further object of the present invention to provide an ear plug which will aid in the treatment and prevention of ear infections by reducing the level of humidity from within the ear canal of a user.

It is also an object of the present invention to provide an ear plug which will create a transitory pressure gradient from a point within the ear canal of a user to a point within the ear plug itself.

These and other objects will become clear upon a reading

DETAILED DESCRIPTION OF THE PREFERRED EMBODIMENT

Figure 1:
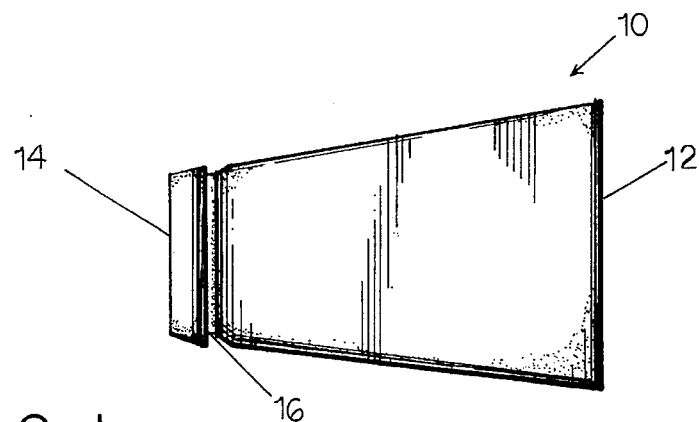
FIG. 1 is a front elevational view of an ear plug according to the present invention.

Reference is made herein to the attached drawing figures. Like reference numerals are used throughout the various drawings to designate like elements of the claimed invention.

Referring to FIG. 1, this drawing depicts a front elevational view of ear plug 10 of the presently claimed invention. The ear plug 10 includes main body 12, removable integral tip 14, and integral groove 16.

Figure 3:
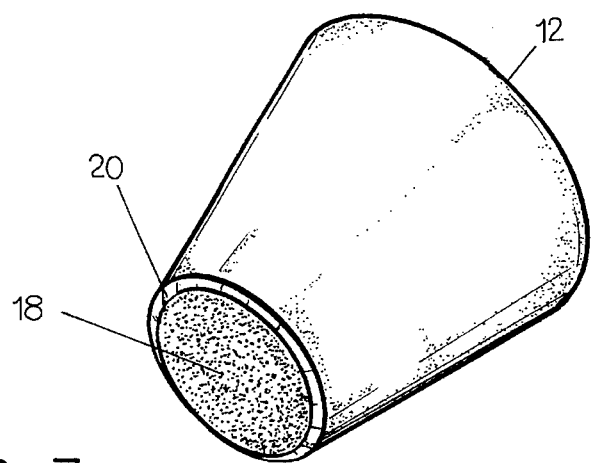
FIG. 3 is a perspective view of the ear plug shown in FIG. 2, with the tip of the ear plug removed.

As more clearly shown in perspective in FIG. 3, the main body 12 of the ear plug is constructed from a resilient, hygroscopic, conical body 18, surrounded by a resilient, water-proof outer casing 20. In the view of FIG. 3, the removable integral tip 14 has been removed to reveal the resilient, hygroscopic, conical body 18. This is how the ear plug appears immediately before use.

Figure 2:
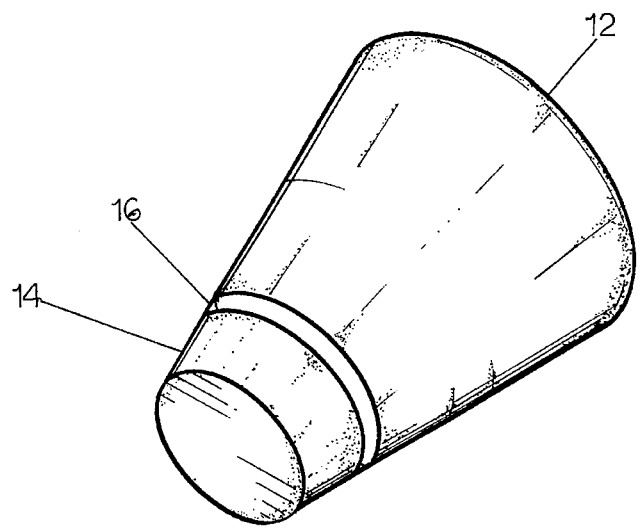
FIG. 2 is a perspective view of the ear plug as seen in FIG. 1.

In storage, the main body 12 and integral tip 14 define a single unitary structure as shown in FIGS. 1 and 2. The resilient, water-proof outer casing (depicted at reference numeral 20 in FIG. 3) completely surrounds and hermetically seals both the resilient, hygroscopic body 18 and the integral tip 14 from the ambient environment.

When the ear plug is to be used, the integral tip 14 is removed from the main body 12 to expose the hygroscopic body 18. The main body 12 is then compressed (normally by rolling with the finger tips), and inserted into the outer ear canal of a user with the hygroscopic body 18 exposed to the ambient environment inside the user's ear canal. The conical body 18 may be made from any suitably flexible and moisture-absorbing material. Included among these are natural foamed rubbers, synthetic foamed rubbers, polyester elastomers, and the like. Foamed rubbers are preferred.

The conical body 18 may also be constructed from a foamed rubber impregnated with a suitable desiccant, such as anhydrous sodium silicate, calcium silicate, calcium carbonate and the like.

Once inserted into the ear canal of a user, the natural resiliency of the main body 12 causes it to expand, and thereby form a friction fit within the ear canal of the user. The expansion of the main body 12 adds to the moisture removing function of the ear plug by creating a small pressure gradient from a point within the ear canal to a point within the main body 12, which tends to draw moisture into the body of the ear plug. This pressure gradient is, of course, transitory, and will eventually be dissipated by air flow through the eustachian tubes. However, if the user is suffering from a particularly acute ear infection, the pressure gradient may persist for extended periods of time due to complete blockage of the eustachian tubes. In either event, the hygroscopic body 18 will absorb moisture from within the ear canal of the user, thereby removing excess moisture from the ear canal.

The water-proof casing may be provided with a non-slick, and hypoallergenic outer finish in order to provide a secure, non-irritating friction fit within the ear of a user. The casing may be made from any suitably flexible, water-proof material, including polyolefin films, polyester films, polyether films, polyacrylic films, polymethacrylic films, polyacrylate films, polymethacrylate films, polyamide films, cellulosic films and the like. Polyolefin films are preferred.

It is to be understood that the invention is not limited in any manner to the embodiment described above, but includes any and all embodiments encompassed by the following claims.

I claim:

1. A moisture absorbing ear plug comprising:

a resilient, hygroscopic body;

an integral tip portion of said hygroscopic body which is removable from said hygroscopic body to expose a surface of said hygroscopic body; and a resilient, water-proof outer casing completely surrounding said hygroscopic body and said integral tip.

2. The moisture absorbing ear plug according to claim 1, wherein said resilient, water-proof outer casing includes a non-slick, hypoallergenic outer surface.

3. The moisture absorbing ear plug according to claim 1, wherein said integral tip is made from the same material as said hygroscopic body.

4. The moisture absorbing ear plug according to claim 1, wherein said hygroscopic body includes a groove which defines said integral tip portion.

5. The moisture absorbing ear plug according to claim 1, wherein said resilient, hygroscopic, body is made from materials selected from the group consisting of natural foamed rubbers, synthetic foamed rubbers, and polyester elastomers.

6. The moisture absorbing ear plug according to claim 1, wherein said resilient, water-proof outer casing is made from materials selected from the group consisting of polyolefin films, polyester films, polyether films, polyacrylic films, polymethacrylic films, polyacrylate films, polymethacrylate films, polyamide films and cellulosic films.

7. A moisture absorbing ear plug comprising:

a resilient, hygroscopic, conical body made from foamed rubber;

an integral foamed rubber tip integral with said conical body and removable therefrom, said conical body and said integral tip defining a groove between said conical body and said integral tip; and a resilient, water-proof outer casing completely surrounding said resilient, hygroscopic conical body and said integral tip; wherein a surface of said resilient, hygroscopic conical body is exposed when said integral tip is removed from said resilient, hygroscopic conical body, whereby insertion of said hygroscopic body into an outer ear canal of an user allows moisture to be drawn from the ear canal through said surface into said hydroscopic body which is then removed and disposed of.

* * * * *